United States Patent
Walsh et al.

(10) Patent No.: US 10,779,967 B2
(45) Date of Patent: Sep. 22, 2020

(54) STENTS WITH DUAL TISSUE-WALL ANCHORING FEATURES

(71) Applicant: Boston Scientific Scimed, Inc., Maple Grove, MN (US)

(72) Inventors: Michael Walsh, Galway (IE); Martyn G. Folan, Galway (IE); Shane Moylan, Galway (IE); Thomas M. Keating, Galway (IE); Martin Hynes, Galway (IE); Thomas Holly, Galway (IE)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 140 days.

(21) Appl. No.: 15/939,410

(22) Filed: Mar. 29, 2018

(65) Prior Publication Data

US 2018/0280166 A1 Oct. 4, 2018

Related U.S. Application Data

(60) Provisional application No. 62/478,998, filed on Mar. 30, 2017.

(51) Int. Cl.
*A61F 2/91* (2013.01)
*A61F 2/848* (2013.01)
*A61F 2/06* (2013.01)
*A61F 2/04* (2013.01)
*A61M 27/00* (2006.01)

(52) U.S. Cl.
CPC .............. *A61F 2/848* (2013.01); *A61F 2/064* (2013.01); *A61F 2/91* (2013.01); *A61F 2002/041* (2013.01); *A61M 27/002* (2013.01)

(58) Field of Classification Search
CPC ...... A61F 2/90; A61F 2/848; A61F 2002/821; A61F 2/064; A61F 2002/041; A61F 2250/007; A61B 2017/00637; A61B 2017/1139; A61M 27/002; A61M 27/004
See application file for complete search history.

(56) References Cited

U.S. PATENT DOCUMENTS

| 2002/0082467 | A1 | 6/2002 | Campbell |
| 2008/0109069 | A1* | 5/2008 | Coleman ............... A61B 17/11 |
| | | | 623/1.25 |
| 2009/0143713 | A1 | 6/2009 | Van Dam et al. |

FOREIGN PATENT DOCUMENTS

| GB | 1593931 A | 7/1981 |
| JP | S5839722 Y2 | 9/1983 |
| WO | 9918887 A1 | 4/1999 |
| WO | 2013004264 A1 | 1/2013 |

OTHER PUBLICATIONS

International Search Report and Written Opinion filed on Mar. 29, 2018 for Application No. PCT/US2018/024996.
Mueller et al., Percutaneous Biliary Drainage: Technical and Catheter Related Problems in 200 Procedures, article in American Journal of Roentgenology (AJR), Jan. 1982, pp. 17-23.

* cited by examiner

*Primary Examiner* — Suba Ganesan

(57) ABSTRACT

The present disclosure relates generally to the field of stents for body lumen drainage. In particular, the present disclosure relates to systems and methods for forming a fluid channel between tissue walls of varying thickness using a stent.

20 Claims, 3 Drawing Sheets

STENTS WITH DUAL TISSUE-WALL ANCHORING FEATURES

CROSS REFERENCE TO RELATED APPLICATIONS

This application claims the benefit of priority under 35 U.S.C. § 119 to U.S. Provisional Patent Application Ser. No. 62/478,998, filed on Mar. 30, 2017, which is incorporated by reference in its entirety for all purposes.

FIELD

The present disclosure relates generally to the field of body lumen drainage. In particular, the present disclosure relates to systems and methods for creating an open flow passage between tissue walls of varying thickness.

BACKGROUND

Drainage of body fluids from within a duct or other location in the body to a collection location outside of body through a path created percutaneously, can have attendant difficulties. For example, bile is yellowish brown fluid produced by the liver and delivered to the small intestine through bile ducts to assist in the digestion of lipids. Bile duct blockages may cause bile to accumulate within the body, resulting in physical manifestations including jaundice, itching and darkened urine. Percutaneous transhepatic biliary drainage is a medical procedure, typically performed when surgical or endoscopic management procedures have failed, in which a flexible plastic tube or self-expanding stent is introduced through the patient's skin into the bile duct to drain bile into a collection bag outside the body or the small intestine. A variety of delayed medical complications tend to follow such procedures, including bile leakage around the insertion site, trauma at the tissue wall anchoring site(s), tube migration, tube dislodgment and/or tube blockage.

A variety of advantageous medical outcomes may be realized by the systems and/or methods of the present disclosure, which provide drainage stents capable of securely anchoring tissue walls of varying thickness to inhibit stent migration and minimize tissue trauma, particularly in the field of minimally invasive devices and procedures for creating an open flow passage between tissue walls of varying thickness.

SUMMARY

In one aspect, the present disclosure relates to a stent comprising an elongate body having a constrained configuration, and an expanded configuration in which a proximal portion of the body expands into a proximal retention member, a distal portion expands into a distal retention member, and a cylindrical saddle region extends between the proximal and distal retention members. The proximal retention member, distal retention member and cylindrical saddle region may define an open interior passage configured to permit flow therethrough. The proximal retention member may include first and second flanges separated from each other by a first distance, and the distal retention member may include third and fourth flanges separated from each other by a second distance, the first distance being greater than the second distance. The proximal retention member, distal retention member and cylindrical saddle region may be formed of a woven material. The proximal and distal retention members may be formed of a woven material and the cylindrical saddle region may be formed of a knitted material. The proximal and distal retention members may be formed of a woven material and the cylindrical saddle region may be formed of a polymeric material. The proximal and distal retention members may be formed of a polymeric material and the cylindrical saddle region may be formed of a woven material. The proximal retention member, distal retention member and/or cylindrical saddle region may be covered. The polymeric material may biodegradable or bioerodible. The second and third flanges may be separated by a third distance, the third distance being greater than the first distance. The first, second, third and fourth flanges may extend perpendicular to a circumference of the elongate body. A diameter of the first, second, third and fourth flanges may be larger than a diameter of the cylindrical saddle region. The first and second flanges may be configured to contact opposite sides of a first tissue layer, and the third and fourth flanges may be configured to contact opposite sides of a second tissue layer. A valve may be disposed within the open interior passage of the elongate body.

In another aspect, the present disclosure relates to a stent comprising a stent body formed of a woven filament having a constrained configuration, and an expanded configuration in which a proximal portion of the body expands into a proximal retention member, a distal portion expands into a distal retention member, and a cylindrical saddle region extends between the proximal and distal retention members. The proximal retention member, distal retention member and cylindrical saddle region may be covered. The proximal retention member, distal retention member and cylindrical saddle region may define an open interior passage configured to permit flow therethrough. The proximal retention member may include first and second flanges separated from each other by a first distance, and the distal retention member may include third and fourth flanges separated from each other by a second distance, the first distance being greater than the second distance. The second and third flanges may be separated by a third distance, the third distance being greater than the first distance. The first, second, third and fourth flanges may extend perpendicular to a circumference of the stent body. A diameter of the first, second, third and fourth flanges may be larger than a diameter of the cylindrical saddle region. The first and second flanges may be configured to contact opposite sides of a first tissue layer, and the third and fourth flanges may be configured to contact opposite sides of a second tissue layer. A valve may be disposed within the open interior passage of the stent body.

In another aspect, the present disclosure relates to a stent comprising an elongate body having a constrained configuration, and an expanded configuration in which a proximal portion of the body expands into a proximal retention member, a distal portion expands into a distal retention member, and a cylindrical saddle region extends between the proximal and distal retention members. The proximal and distal retention members may be formed of a woven material and the cylindrical saddle region may be formed of a knitted material. The proximal retention member, distal retention member and/or cylindrical saddle region may be covered. The proximal retention member, distal retention member and cylindrical saddle region may define an open interior passage configured to permit flow therethrough. The proximal retention member may include first and second flanges separated from each other by a first distance, and the distal retention member may include third and fourth flanges separated from each other by a second distance, the first distance being greater than the second distance. The second and third flanges may be separated by a third distance, the third distance being greater than the first distance. The first, second, third and fourth flanges may extend perpendicular to a circumference of the elongate body. A diameter of the first, second, third and fourth flanges may be larger than a diameter of the cylindrical saddle region. The first and second flanges may be configured to contact opposite sides of a first tissue layer, and the third and fourth flanges may be configured to contact opposite sides of a second tissue layer. A valve may be disposed within the open interior passage of the elongate body.

In yet another aspect, the present disclosure relates to a stent comprising an elongate body having a constrained configuration, and an expanded configuration in which a proximal portion of the body expands into a proximal retention member, a distal portion expands into a distal retention member, and a cylindrical saddle region extends between the proximal and distal flanges. The proximal and distal retention members may be formed of a woven material and the cylindrical saddle region may be formed of a polymeric material. The proximal and/or distal retention members may be covered. The proximal retention member, distal retention member and cylindrical saddle region may define an open interior passage configured to permit flow therethrough. The proximal retention member may include first and second flanges separated from each other by a first distance, and the distal retention member may include third and fourth flanges separated from each other by a second distance, the first distance being greater than the second distance. The second and third flanges may be separated by a third distance, the third distance being greater than the first distance. The first, second, third and fourth flanges may extend perpendicular to a circumference of the elongate body. A diameter of the first, second, third and fourth flanges may be larger than a diameter of the cylindrical saddle region. The first and second flanges may be configured to contact opposite sides of a first tissue layer, and the third and fourth flanges may be configured to contact opposite sides of a second tissue layer. A valve may be disposed within the open interior passage of the stent body. The cylindrical saddle region may include an internal or external support structure. The cylindrical saddle region may include one or more corrugated portions.

In yet another aspect, the present disclosure relates to a stent comprising an elongate body having a constrained configuration, and an expanded configuration in which a proximal portion of the body expands into a proximal retention member, a distal portion expands into a distal retention member, and a cylindrical saddle region extends between the proximal and distal flanges. The proximal and distal retention members may be formed of a polymeric material and the cylindrical saddle region may be formed of a woven material. The cylindrical saddle region may be covered. The proximal retention member, distal retention member and cylindrical saddle region may define an open interior passage configured to permit flow therethrough. The proximal retention member may include first and second flanges separated from each other by a first distance, and the distal retention member may include third and fourth flanges separated from each other by a second distance, the first distance being greater than the second distance.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures.

DETAILED DESCRIPTION

The present disclosure is not limited to the particular embodiments described. The terminology used herein is for the purpose of describing particular embodiments only, and is not intended to be limiting beyond the scope of the appended claims. Unless otherwise defined, all technical terms used herein have the same meaning as commonly understood by one of ordinary skill in the art to which the disclosure belongs.

Finally, although embodiments of the present disclosure are described with specific reference to medical devices and systems for drainage of the bile duct, it should be appreciated that such medical devices may be used to establish and/or maintain a temporary or permanent open flow passage between a variety of body organs, lumens and spaces, e.g., the dermis, stomach, duodenum, kidneys and gall bladder. The devices can be inserted via different access points and approaches, e.g., percutaneously, endoscopically, laparoscopically or some combination. The stent described are self-expanding, but other embodiments where the stent is expandable by other means, for example, a balloon catheter, may be possible. Moreover, such medical devices are not limited to drainage, but may facilitate access to organs for other purposes, such as removing obstructions and delivering therapy, including non-invasive or minimally invasive manipulation of the tissue within the organ and/or the introduction of pharmacological agents via the open flow passage.

As used herein, the singular forms "a," "an," and "the" are intended to include the plural forms as well, unless the context clearly indicates otherwise. It will be further understood that the terms "comprises" and/or "comprising," or "includes" and/or "including" when used herein, specify the presence of stated features, regions, steps elements and/or components, but do not preclude the presence or addition of one or more other features, regions, integers, steps, operations, elements, components and/or groups thereof.

As used herein, the term "distal" refers to the end farthest away from the medical professional when introducing a device into a patient, while the term "proximal" refers to the end closest to the medical professional when introducing a device into a patient.

Figure 1A:
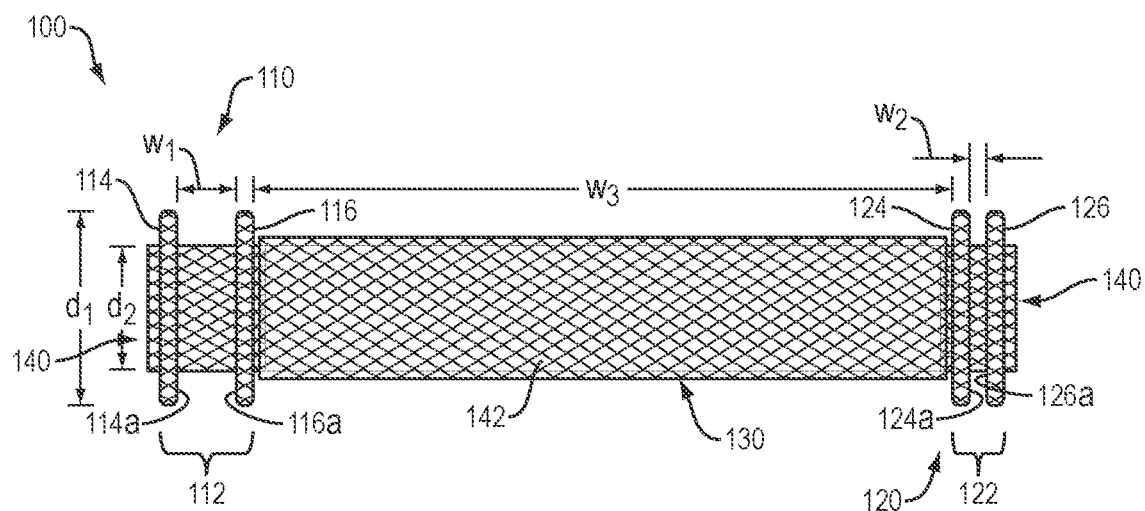
FIG. 1A provides a perspective view of a self-expanding drainage stent, according to one embodiment of the present disclosure.

In one embodiment, the present disclosure relates to a self-expanding drainage stent configured to extend between separate tissue layers. Referring to FIG. 1A, in one embodiment, a drainage stent of the present disclosure may include an elongate body 100 formed of a woven, knitted or braided filament (e.g., nitinol, etc.) and configured to move between a constrained configuration and an expanded configuration. In the expanded configuration, a proximal portion 110 of the elongate body 100 may form a proximal retention member 112 comprising first and second flanges 114, 116, a distal portion 120 of the elongate body 100 may form a distal retention member 122 comprising third and fourth flanges 124, 126, with a cylindrical saddle region 130 extending between the proximal and distal retention members. The proximal retention member, distal retention member and/or cylindrical saddle region may include a coating 142 on an inner and/or outer surface thereof to define a contiguous open interior passage 140 configured for flow (e.g., body fluids, materials, and the like) therethrough. The coating 142 may comprise a variety of non-degradable and biocompatible polymeric materials (e.g., upon exposure to bodily fluids such as bile), including, for example, silicones, rubbers, polyethylenes, PVDF, Chronoflex® and thermoplastic elastomers. The first and second flanges 114 and 116 may be separated by a first distance $W_1$, and the third and fourth flanges 124, 126 may be separated by a second distance $W_2$, with the first distance $W_1$ being greater than the second distance $W_2$. The second and third flanges 116, 124 may be separated by a third distance $W_3$ to define a length of the saddle region 130. By way of non-limiting example, the first distance $W_1$ may be approximately 25.0 mm (e.g., at least 15.0 mm, at least 20.0 mm, at least 30.0 mm, at least 35.0 mm, etc.), the second distance may be approximately 0.5 mm (e.g., at least 0.25 mm, at least 0.75 mm, at least 1.00 mm, etc.). The third distance $W_3$ may be less than the first distance $W_1$ but greater than the second distance $W_2$. For example, the third distance $W_3$ may be approximately 10.0 mm (e.g., at least 5.0 mm, at least 15.0 mm, etc.). Alternatively, the third distance $W_3$ may be greater than the first distance $W_1$. For example, the third distance $W_3$ may be approximately 200.0 (e.g., at least 50.0, at least 100.0, at least 150.0, at least 250.0, etc.). Each of the first, second, third and fourth flanges 114, 116, 124, 126 may extend perpendicular to a circumference of the elongate body 100 to define respective planar surfaces 114a, 116a, 124a, 126a. In various embodiments, the first, second, third and fourth flanges may include various configurations, such that one or more of the flanges extend radially at an angle that is not necessarily perpendicular to the elongate body and/or the surfaces 114a, 116a, 124a and/or 126a are not necessarily planar. For example, any or all of the first, second, third and fourth flanges may extend outward towards an end of the elongate body, back towards a center portion of the elongate body, or change directions in some combination of both.

In various embodiments, the first distance $W_1$ may be sufficient for the planar surfaces 114a, 116a of the first and second flanges 114, 116 to contact and firmly compress (e.g., engage) opposite sides of a first tissue wall, such as, e.g., the abdominal wall. The second distance $W_2$ may be sufficient for the planar surfaces 124a, 126a of the third and fourth flanges 124, 126 to contact and firmly compress (e.g., engage) opposite sides of a second tissue wall, such as, e.g., the bile duct. One or more of the planar surfaces 114a, 116a, 124a, 126a may further include a surface pattern (e.g., bumps, projections, knobs, etc.) arranged in a variety of random or non-random patterns to engage the respective tissue wall to limit or prevent movement (e.g., rotation) of the stent within or between the tissue walls. The third distance $W_3$ may be sufficient to allow the cylindrical saddle region to extend between the first and second tissue walls to provide an open interior passage therebetween, without exerting undue tension on or between either tissue wall. In one embodiment, the portion of the elongate body 100 which forms the cylindrical saddle region 130 may be configured such that is does not foreshorten as either of the proximal or distal retention members are deployed, thereby minimizing tension applied between the first and second tissue walls. Each of the first, second, third and fourth flanges 114, 116, 124, 126 may include an outer diameter $d_1$ that is greater than an outer diameter $d_2$ of the cylindrical saddle region and/or the portion of the proximal and distal retention members 112, 122 between the respective flanges 114, 116, 124, 126. For example, outer diameter $d_1$ may be approximately 7.0 mm to approximately 30 mm, and outer diameter $d_2$ may be approximately 3.0 mm to approximately 15.0 mm. For example, in one or more embodiments, one or more of the first, second, third and fourth flanges 114, 116, 124, 126 may include an outer diameter $d_1$ that is as much as 75%-100% greater than an outer diameter $d_2$ of the cylindrical saddle region and/or the portion of the proximal and distal retention members 112, 122 between the respective flanges 114, 116, 124, 126.

Figure 1B:
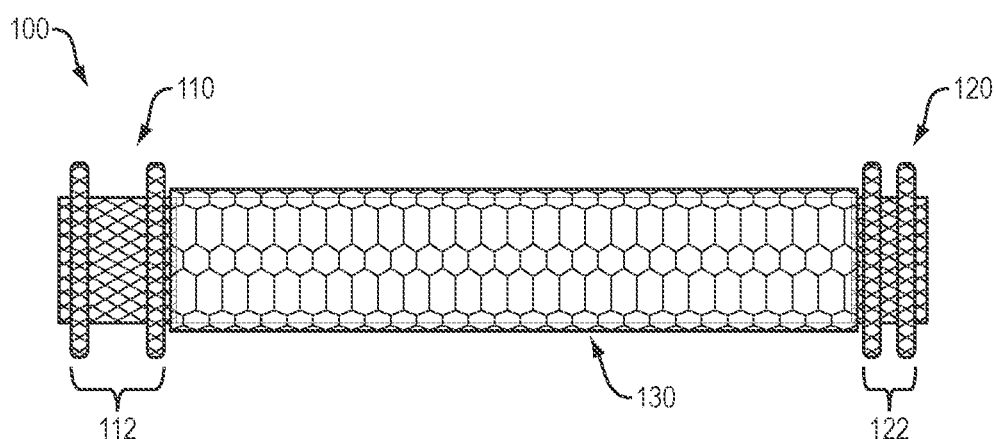
FIG. 1B provides a perspective view of a self-expanding drainage stent, according to one embodiment of the present disclosure.

Referring to FIG. 1B, in one embodiment, the first and second portions 110, 120 of the elongate body 100 may be formed of a woven or braided filament (e.g., nitinol) configured to form proximal and distal retention members 112, 122 as discussed above, and the cylindrical saddle region 130 may be formed of a knitted filament (e.g., nitinol, etc.). As compared to a woven or braided filament, the knitted filament may impart a greater degree of flexibility to the cylindrical saddle region, thereby reducing the likelihood of one or both retention members becoming dislodged or otherwise applying excessive force to either tissue wall as the patient moves. In one embodiment, the respective ends of the cylindrical saddle 130 region may be affixed (e.g., adhered, bonded, interwoven, attached, etc.) to the proximal and distal portions 110, 120 using suitable glues, adhesives, resins or other bonding techniques. Alternatively, the weave of the cylindrical saddle region can be made different than the weave of the proximal and distal portions to impart a greater degree of flexibility to the saddle region. For example, the weave pattern and/or the pitch of the weave of the saddle regions can be adjusted as necessary for the flexibility desired.

Figure 1C:
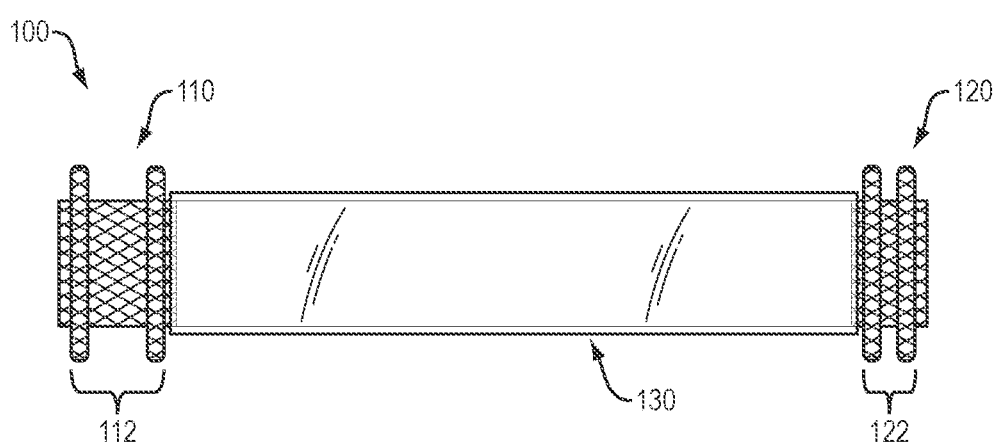
FIG. 1C provides a perspective view of a self-expanding drainage stent, according to one embodiment of the present disclosure.

Referring to FIG. 1C, in one embodiment, the first and second portions 110, 120 of the elongate body 100 may be formed of a woven or braided filament (e.g., nitinol) configured to form proximal and distal retention members 112, 122 as discussed above, and the cylindrical saddle region 130 may be formed of a polymeric material (e.g., polyethylene terephthalate (PET), silicone, shape memory thermoplastics and/or thermosets, etc.). Alternatively, a portion of the cylindrical saddle region may be formed from a polymeric material, and another portion of the cylindrical saddle region may be formed from a woven, braided or knitted filament. In various embodiments, the polymeric material may impart sufficient flexibility or malleability to the cylindrical saddle region, or a portion thereof, such that the proximal and distal retention members may engage nonaligned openings in tissue walls without exerting undue pressure or strain on either tissue wall. In addition, or alternatively, the cylindrical saddle region may include a variety of internal or external support structures (e.g., helical support structures, spiral support structures, corrugated sections, etc.) to impart increased flexibility between the proximal and distal retention members.

Figure 1D:
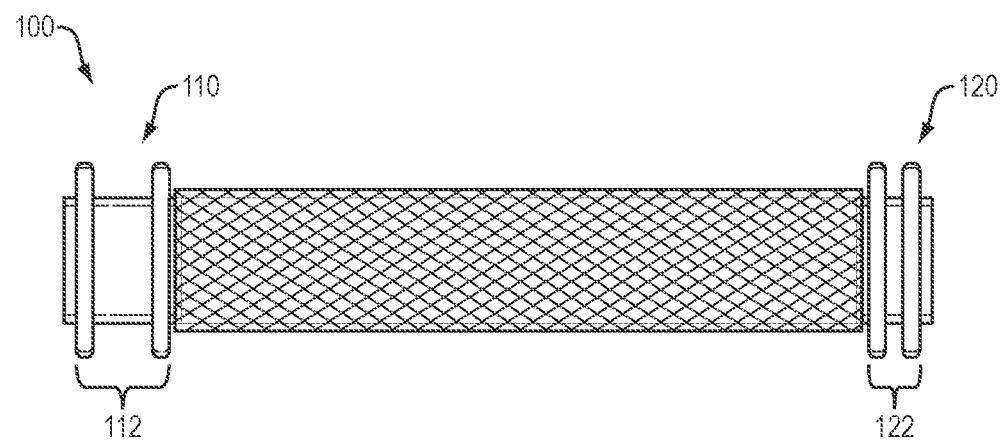
FIG. 1D provides a perspective view of a self-expanding drainage stent, according to one embodiment of the present disclosure.

Referring to FIG. 1D, in one embodiment, the proximal and distal portions 110, 120 of the elongate body 100 may be formed of a polymeric material (e.g., polyethylene terephthalate (PET), silicone, shape memory thermoplastics and/or thermosets, etc.) configured to form proximal and distal retention members 112, 122, and the cylindrical saddle region 130 may be formed of a woven or braided filament (e.g., nitinol).

In various embodiments, the polymeric material may include a biodegradable or bioerodible material configured to allow the proximal and/or distal retention members to partially or completely degrade over time, such that the stent is released from the first and second tissue walls without requiring surgical intervention. In either of the embodiments of FIGS. 1C-1D, the woven or braided filament may be affixed to the polymeric material using suitable glues, adhesives, resins or other bonding techniques. In addition, or alternatively, the braided filament in any of the various embodiments may be metal filament or polymer filament, and may further include a single filament woven upon itself or multiple filaments woven together.

Figure 1E:
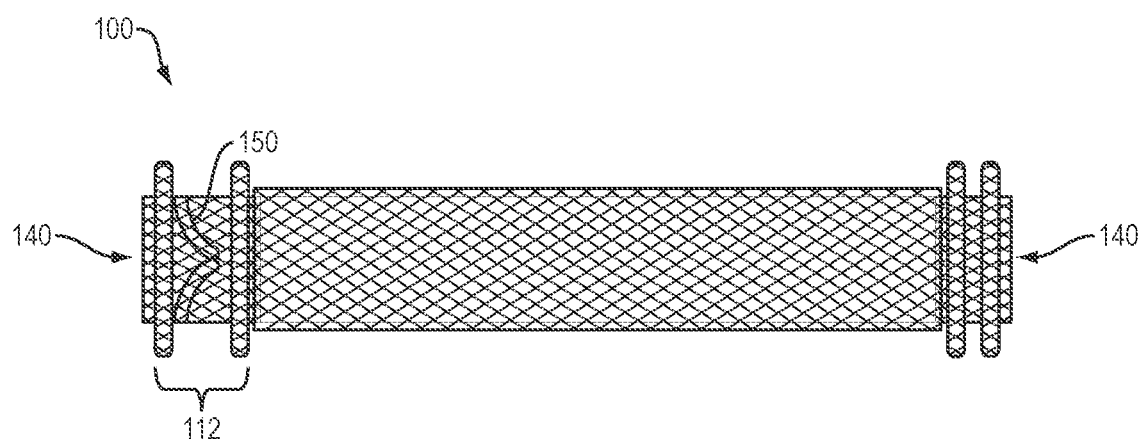
FIG. 1E provides a perspective view of a self-expanding drainage stent, according to one embodiment of the present disclosure.

Referring to FIG. 1E, in one embodiment, the open interior passage 140 of the elongate body 100 may further include one or more valves 150 (e.g., duck-bill valve, slit valve, etc.) moveable between closed and open configurations to block or prevent the flow of fluids therethrough, until the patient or medical professional determines that the valve should be opened (e.g., by inserting a drainage tube). Although the valve 150 is depicted within the first retention member 112, in various embodiments the valve 150 may be positioned anywhere along the open interior passage 140 of the elongate body 100. Examples of such valves are described in U.S. Patent Publication No. 2012/0226243, the contents of which is hereby incorporated by reference in its entirety. Such valves may comprise a variety of suitable biocompatible and non-degradable materials, including any of the polymers discussed herein, and may be utilized with any of the various embodiments described or otherwise contemplated as within the scope of the present disclosure.

Figure 1F:
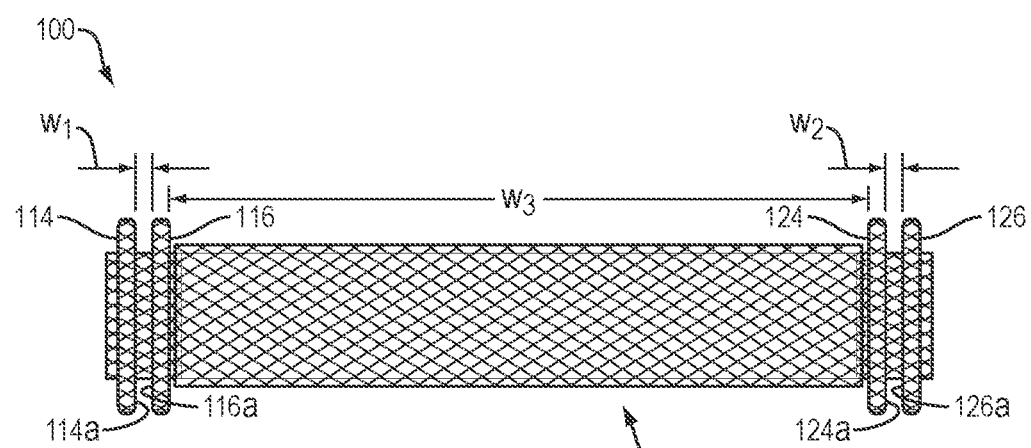
FIG. 1F provides a perspective view of a self-expanding drainage stent, according to one embodiment of the present disclosure.

Referring to FIG. 1F, in one embodiment, the first and second flanges 114 and 116 of the proximal retention member of the elongate body 100 may be separated by a first distance $W_1$, and the third and fourth flanges 124, 126 of the distal retention member may be separated by a second distance $W_2$, with the first distance and the second distances being substantially the same. The second and third flanges 116, 124 may be separated by a third distance $W_3$ to define a length of the saddle region 130. For example, the first distance $W_1$ and second distance $W_2$ may both be approximately 0.5 mm (e.g., at least 0.25 mm, at least 0.75 mm, at least 1.00 mm, etc.). In various embodiments, the first distance $W_1$ may be sufficient for the planar surfaces 114a, 116a of the first and second flanges 114, 116 to contact and firmly compress (e.g., engage) opposite sides of a first tissue wall, such as, e.g., the duodenum wall. The second distance $W_2$ may be sufficient for the planar surfaces 124a, 126a of the third and fourth flanges 124, 126 to contact and firmly compress (e.g., engage) opposite sides of a second tissue wall, such as, e.g., the bile duct. The third distance $W_3$ may be sufficient to for the cylindrical saddle region to extend between the first and second tissue walls to provide an open interior passage therebetween without exerting undue tension on or between either tissue wall. In various embodiments, the first, second, third and fourth flanges may include various configurations, such that one or more of the flanges extend radially at an angle that is not necessarily perpendicular to the elongate body and/or the surfaces 114a, 116a, 124a and/or 126a are not necessarily planar. For example, any or all of the first, second, third and fourth flanges may extend outward towards an end of the elongate body, back towards a center portion of the elongate body, or change directions in some combination of both.

Figure 2:
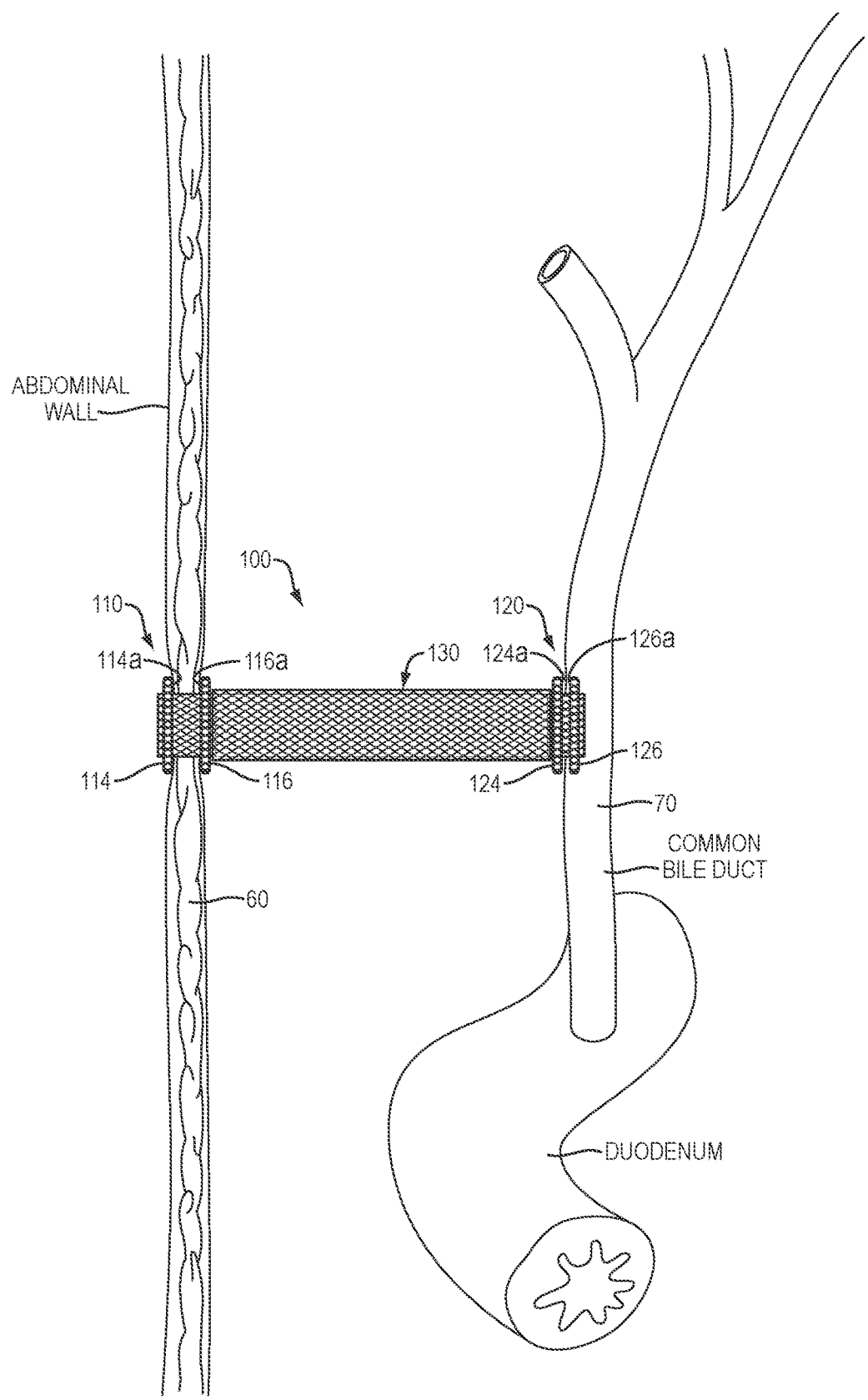
FIG. 2 provides a perspective view of the self-expanding drainage stent of FIG. 1A disposed within a patient, according to one embodiment of the present disclosure.

Referring to FIG. 2, in one embodiment, a drainage stent 100 of the present disclosure may be positioned within a patient such that the planar surfaces 114a, 116a of the first and second flanges 114, 116 contact (e.g., engage) opposite sides of the abdominal wall 60, the planar surfaces 124a, 126a of the third and fourth flanges 124, 126 contact opposite sides of the bile duct 70 and the cylindrical saddle region 130 extends between abdominal wall and bile duct to provide an open interior passage therebetween.

In use and by way of example, the drainage stent may be disposed in the constrained configuration within the lumen of a tissue-penetrating element. A sharpened distal end of the tissue penetrating element may be advanced through the abdominal wall and into an interior region of the bile duct. The distal portion 120 of the stent body 100 may then be advanced distally beyond the lumen of the tissue-penetrating element such that the fourth flange 126 is deployed within the bile duct and the planar surface 126a placed in contact with the inner wall thereof. The tissue-penetrating element may then be proximally retracted such that the sharpened distal end is disposed outside the bile duct, and the remaining distal portion 120 of the elongate body advanced distally beyond the lumen of the tissue-penetrating element such that the third flange 124 is deployed outside the bile duct and the planar surface 124a placed in contact with the outer wall thereof.

With the distal retention member fully deployed, the tissue-penetrating member may be proximally retracted such that the sharpened distal end is disposed adjacent to the inner surface of the abdominal wall. The proximal portion 110 of the stent body 110 may then be advanced distally beyond the lumen of the tissue-penetrating element such that the second flange is deployed to place the planar surface 116a in contact with the inner abdominal wall. The tissue-penetrating element may then be proximally retracted such that the sharpened distal end is disposed outside the patient, and the remaining proximal portion 110 of the elongate body advanced distally beyond the lumen of the tissue-penetrating element such that the first flange is deployed to place the planar surface 114a in contact with the outer abdominal wall.

Alternatively, in the method above, a separate instrument with a sharpened distal tip may be advanced along the path above and into the bile duct to create a path, a guidewire put in place and the separate instrument withdrawn over the guidewire, and a drainage stent, according to the various embodiments described above, loaded on a delivery catheter inserted over the guidewire, and the stent then deployed according to the steps outlined above.

In various embodiments, medical devices (e.g., collection bags, etc.) may be attached to the portion of the stent body 100 extending outside the patient's body. In addition, or alternatively, a variety of medical devices may be inserted through the open interior passage defined by the stent body in the expanded configuration. For example, a drainage tube may be advanced through the open interior passage to facilitate drainage of fluids therethrough. Alternatively, a retrieval device may be introduced through the open interior passage to remove an obstruction (e.g., gallstones, etc.) from within the bile duct.

All of the devices and/or methods disclosed and claimed herein can be made and executed without undue experimentation in light of the present disclosure. While the devices and methods of this disclosure have been described in terms of preferred embodiments, it may be apparent to those of skill in the art that variations can be applied to the devices and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

What is claimed is:

1. A stent, comprising:
   a stent body formed of a woven filament having a constrained configuration,
   the stent body having an expanded configuration with a proximal portion of the body expanded into a proximal retention member, a distal portion expanded into a distal retention member, and a cylindrical saddle region extending between the proximal and distal retention members;
   wherein the proximal retention member, distal retention member and cylindrical saddle region define an open interior passage configured to permit flow therethrough; and
   wherein the proximal retention member includes first and second flanges separated from each other by a first distance, and the distal retention member includes third and fourth flanges separated from each other by a second distance, the first distance being greater than the second distance;
   wherein the first, second, third, and fourth flanges are the same shape.

2. The stent of claim 1, wherein the second and third flanges are separated by a third distance, the third distance being greater than the first distance.

3. The stent of claim 1, wherein the first, second, third and fourth flanges comprise planar surfaces extending perpendicular to a circumference of the stent body.

4. The stent of claim 1, wherein a diameter of the first, second, third and fourth flanges is larger than a diameter of the cylindrical saddle region.

5. The stent of claim 1, wherein the first and second flanges are configured to contact opposite sides of a first tissue layer, and the third and fourth flanges are configured to contact opposite sides of a second tissue layer.

6. The stent of claim 1, further comprising a valve disposed within the open interior passage of the stent body.

7. A stent, comprising:
   an elongate body having a constrained configuration,
   the elongate body having an expanded configuration with a proximal portion of the body expanded into a proximal retention member, a distal portion expanded into a distal retention member, and a cylindrical saddle region extending between the proximal and distal retention members;
   the proximal and distal retention members formed of a woven material and the cylindrical saddle region formed of a knitted material;
   wherein the proximal retention member, distal retention member and cylindrical saddle region define an open interior passage configured to permit flow therethrough; and
   wherein the proximal retention member includes first and second flanges separated from each other by a first distance, and the distal retention member includes third and fourth flanges separated from each other by a second distance, the first distance being greater than the second distance;
   wherein the first, second, third, and fourth flanges are the same shape.

8. The stent of claim 7, wherein the second and third flanges are separated by a third distance, the third distance being greater than the first distance.

9. The stent of claim 7, wherein the first, second, third and fourth flanges comprise planar surfaces extending perpendicular to a circumference of the elongate body.

10. The stent of claim 7, wherein a diameter of the first, second, third and fourth flanges is larger than a diameter of the cylindrical saddle region.

11. The stent of claim 7, wherein the first and second flanges are configured to contact opposite sides of a first tissue layer, and the third and fourth flanges are configured to contact opposite sides of a second tissue layer.

12. The stent of claim 7, further comprising a valve disposed within the open interior passage of the elongate body.

13. A stent, comprising:
   an elongate body having a constrained configuration,
   the elongate body having an expanded configuration with a proximal portion of the body expanded into a proximal retention member, a distal portion expanded into a distal retention member, and a cylindrical saddle region extending between the proximal and distal flanges;
   the proximal and distal retention members formed of a woven material and the cylindrical saddle region formed of a polymeric material;
   wherein the proximal retention member, distal retention member and cylindrical saddle region define an open interior passage configured to permit flow therethrough; and
   wherein the proximal retention member includes first and second flanges separated from each other by a first distance, and the distal retention member includes third and fourth flanges separated from each other by a second distance, the first distance being greater than the second distance;
   wherein the first, second, third, and fourth flanges are the same shape.

14. The stent of claim 13, wherein the second and third flanges are separated by a third distance, the third distance being greater than the first distance.

15. The stent of claim 13, wherein the first, second, third and fourth flanges comprise planar surfaces extending perpendicular to a circumference of the elongate body.

16. The stent of claim 13, wherein a diameter of the first, second, third and fourth flanges is larger than a diameter of the cylindrical saddle region.

17. The stent of claim 13, wherein the first and second flanges are configured to contact opposite sides of a first tissue layer, and the third and fourth flanges are configured to contact opposite sides of a second tissue layer.

18. The stent of claim 13, further comprising a valve disposed within the open interior passage of the stent body.

19. The stent of claim 13, wherein the cylindrical saddle region includes an internal or external support structure.

20. The stent of claim 13, wherein the cylindrical saddle region includes one or more corrugated portions.

* * * * *